United States Patent [19]
Nagata et al.

[11] Patent Number: 5,856,561
[45] Date of Patent: Jan. 5, 1999

[54] BISPHENOL CARBOXYLIC ACID TERTIARY ESTER DERIVATIVES AND CHEMICALLY AMPLIFIED POSITIVE RESIST COMPOSITIONS

[75] Inventors: Takesi Nagata; Satoshi Watanabe; Katsuya Takemura; Tsunehiro Nishi; Shigehiro Nagura, all of Niigata-ken; Akinobu Tanaka, Fujisawa; Yoshio Kawai, Isehara, all of Japan

[73] Assignees: Shin-Etsu Chemical Co., Ltd.; Nippon Telegraph and Telephone Corp., both of Tokyo, Japan

[21] Appl. No.: 710,298

[22] Filed: Sep. 17, 1996

[30] Foreign Application Priority Data

Sep. 18, 1995 [JP] Japan ...................................... 7-263457

[51] Int. Cl.$^6$ .................................................... C07C 69/76
[52] U.S. Cl. ........................................... 560/57; 430/270.1
[58] Field of Search ............................. 560/57; 430/270.1

[56] References Cited

PUBLICATIONS

Chem. Abst. CA 123:9157 Mar. 14, 1995.
Chem Abst. CA 122:105438 Oct. 11, 1994.

Primary Examiner—Paul J. Killos
Attorney, Agent, or Firm—Millen, White, Zelano & Branigan, P.C.

[57] ABSTRACT

Novel bisphenol carboxylic acid tertiary ester derivatives having two aromatic ether groups and an ester group which are all replaced by acid labile groups are provided. The derivatives are used as a dissolution inhibitor in a chemically amplified positive resist composition comprising an organic solvent, an alkali soluble resin, and a photo-acid generator. Since the dissolution inhibitor has a highly reactive acetal group as an acid labile group, its coupling-off rapidly takes place after exposure. The dissolution inhibitor itself is less alkali soluble and its acid decomposition product is a phenol derivative having a carboxylic acid group with high alkali solubility, leading to a high dissolution contrast.

14 Claims, No Drawings

BISPHENOL CARBOXYLIC ACID TERTIARY ESTER DERIVATIVES AND CHEMICALLY AMPLIFIED POSITIVE RESIST COMPOSITIONS

BACKGROUND OF THE INVENTION

1. Field of the Invention

This invention generally relates to a chemically amplified positive resist composition which is highly sensitive to actinic radiation such as deep-UV, electron beam and X-ray, can be developed with alkaline aqueous solution to form a pattern, and is thus suitable for use in a fine patterning technique. More particularly, it relates to a bisphenol carboxylic acid tertiary ester derivative which is useful as a dissolution inhibitor in such chemically amplified positive resist compositions.

2. Prior Art

As the LSI technology tends toward higher integration and higher speed, further refinement of pattern rules is required. The current patterning technology mostly relies on light exposure which is now approaching the essential limit of resolution which is dictated by the wavelength of a light source. It is generally recognized that in light exposure using g-line (wavelength 436 nm) or i-line (wavelength 365 nm) as a light source, a pattern rule of about 0.5 µm is the limit. For LSIs fabricated by such light exposure technique, a degree of integration equivalent to 16 mega-bit DRAM is the limit. At present, LSIs fabricated in the laboratory have reached this stage. It is urgently required to develop a finer patterning technique.

Under such circumstances, deep-ultraviolet lithography is regarded promising as the next generation of fine patterning technology. The deep-UV lithography is capable of working on the order of 0.3 or 0.4 µm. If a less light absorbing resist is used, it is possible to form a pattern having a side wall nearly perpendicular to the substrate. Attention is now paid to the technique of utilizing a high illuminance KrF excimer laser as a light source for deep-UV. In order that an excimer laser be utilized in mass-scale manufacture, a resist material featuring low light absorption and high sensitivity is desired.

Chemically amplified, positive working resist materials using acid catalysts were recently developed as disclosed in JP-B 27660/1990, JP-A 27829/1988, U.S. Pat. No. 4,491,628 and No. 5,310,619. These materials have high sensitivity, resolution and dry etching resistance and are promising as resist materials especially suited for deep-UV lithography.

With respect to the chemically amplified positive resist materials, it is known that their function is largely governed by the dissolution inhibitor used. One typical example of the known dissolution inhibitors is given below.

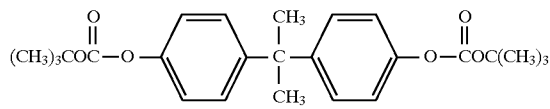

This compound itself is an oil soluble compound. When it is blended as one component of resist material, it serves for three functions of reducing the solubility of the resist material in aqueous base, suppressing film thinning upon development, and in exposed areas, releasing an acid-labile group in the presence of an acid generated so that the resist material becomes soluble in an alkaline developer to increase the dissolution rate of exposed areas.

Chemically amplified positive resist materials using the above-specified compound as a dissolution inhibitor, however, fail to provide high resolution upon alkaline development and undergo profile deterioration due to scum generation. The following two facts account for these drawbacks.

First, decomposition of an acid-labile group is insufficient even after exposure. In the above-specified compound, the acid-labile group which protects phenol is a tert-butoxycarbonyl group. Since this protective group has relatively low acid lability, acid decomposition can be insufficient even after exposure when the above-specified compound is combined with particular resist components.

Secondly, the difference in alkali dissolution rate between the above-specified compound and its acid decomposed product is not so significant. It is noted that the ratio of alkali dissolution rate of the latter to the former is referred to as a dissolution contrast. Since the acid decomposed product of the above-specified compound is a phenol derivative, its increase of dissolution rate in aqueous base is insufficient as compared with carboxylic acid derivatives.

JP-A 167811/1994 discloses a dissolution inhibitor of a similar structure to formula (1) to be defined below in which the hydrogen atom of carboxylic acid is replaced by an alkoxyalkyl, cyclic ether, vinyloxyalkyl or tert-alkoxycarbonylalkyl group. This dissolution inhibitor, however, is unstable in resist material in the presence of a phenolic alkali-soluble resin (that is, under faintly acidic conditions).

SUMMARY OF THE INVENTION

Therefore, an object of the invention is to provide a novel bisphenol carboxylic acid tertiary ester derivative suitable for use in a high-resolution chemically amplified positive resist material adapted for fine processing technology.

Another object of the invention is to provide a chemically amplified positive resist composition containing the derivative as a dissolution inhibitor.

We have found that a bisphenol carboxylic acid tertiary ester derivative having two acid labile group-substituted aromatic ether groups and an acid labile group-substituted ester group as represented by the following general formula (1) is suitable as a dissolution inhibitor for use in a high-resolution chemically amplified positive resist material adapted for fine processing technology and exerts its best performance especially in deep-UV lithography.

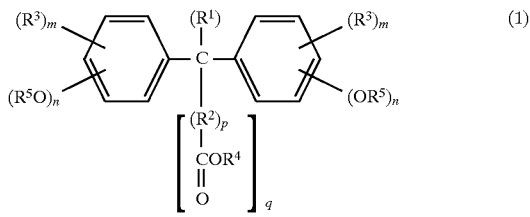

Each of $R^1$ and $R^3$ is a hydrogen atom, normal or branched alkyl group, normal or branched alkoxy group, or normal or branched alkoxyalkyl group; $R^2$ is a normal or branched alkylene group; $R^4$ is a tertiary alkyl group; $R^5$ is an acetal substituent of the following general formula (2):

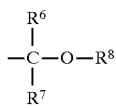

wherein $R^6$ is a hydrogen atom, normal or branched alkyl group, normal or branched alkoxy group, or normal or branched alkoxyalkyl group, which may contain a carbonyl group in their molecular chain, $R^7$ is a normal or branched alkyl group, normal or branched alkoxy group, or normal or branched alkoxyalkyl group, which may contain a carbonyl group in their molecular chain, $R^8$ is a normal or branched alkyl group, or normal or branched alkoxyalkyl group, which may contain a carbonyl group in their molecular chain; and letter p is an integer of 0 to 5, q is equal to 1 or 2, m and n are integers satisfying $m \geq 0$, $n \geq 1$, and $m+n \leq 5$.

More particularly, the bisphenol carboxylic acid tertiary ester derivative serving as a dissolution inhibitor according to the invention has a phenol protective group which has greater acid lability so that this acid labile group is effectively decomposed by the acid generated upon exposure to actinic radiation and the action of post-exposure baking (PEB). The dissolution inhibitor's own alkali solubility is low while its acid decomposed product is a phenol derivative having a carboxylic acid group characterized by high alkali solubility. As a consequence, a greater dissolution contrast is accomplished. The novel derivative according to the invention functions well as a dissolution inhibitor for chemical amplification positive working resist materials, enabling production of a resist image featuring high resolution and a wide range of focal depth.

DETAILED DESCRIPTION OF THE INVENTION

The novel bisphenol carboxylic acid tertiary ester derivative of the invention is a compound of the following general formula (1):

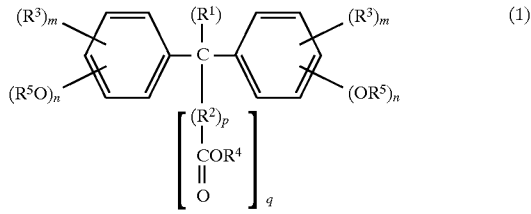

wherein each of $R^1$ and $R^3$ is a hydrogen atom, normal or branched alkyl group, normal or branched alkoxy group or normal or branched alkoxyalkyl group,
$R^2$ is a normal or branched alkylene group,
$R^4$ is a tertiary alkyl group,
$R^5$ is an acetal substituent of the following general formula (2):

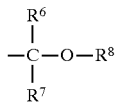

wherein $R^6$ is a hydrogen atom, normal or branched alkyl group, normal or branched alkoxy group, or normal or branched alkoxyalkyl group, which may contain a carbonyl group in their molecular chain, $R^7$ is a normal or branched alkyl group, normal or branched alkoxy group, or normal or branched alkoxyalkyl group, which may contain a carbonyl group in their molecular chain, $R^8$ is a normal or branched alkyl group, or normal or branched alkoxyalkyl group, which may contain a carbonyl group in their molecular chain, and letter p is an integer of 0 to 5, q is equal to 1 or 2, m and n are integers satisfying $m \geq 0$, $n \geq 1$, and $m+n \leq 5$.

In formula (1), the normal or branched alkyl group includes those having 1 to 8 carbon atoms, for example, methyl, ethyl, propyl, isopropyl, n-butyl, sec-butyl, tert-butyl, hexyl, and cyclohexyl groups, with the methyl, ethyl, isopropyl and tert-butyl groups being preferred.

The normal or branched alkoxy group includes those having 1 to 8 carbon atoms, for example, methoxy, ethoxy, propoxy, isopropoxy, n-butoxy, sec-butoxy, tert-butoxy, hexyloxy, cyclohexyloxy, and pyranyloxy groups, with the methoxy, ethoxy, isopropoxy, tert-butoxy, and pyranyloxy groups being preferred.

The normal or branched alkoxyalkyl group includes those having 3 to 10 carbon atoms, for example, methoxyethyl, ethoxypropyl, propoxyethyl, tert-butoxyethyl, acetoxyethyl, and tert-butoxycarbonyloxyethyl groups, with the methoxymethyl, methoxyethyl, ethoxypropyl, and propoxyethyl groups being preferred.

The normal or branched alkylene group includes those having 1 to 8 carbon atoms, for example, methylene, ethylene, propylene, butylene, 2-methylpropylene, and 2-methyl-3-ethoxybutylene groups, with the methylene, ethylene, and propylene groups being preferred.

Included in the tertiary alkyl group are those having 4 to 8 carbon atoms, for example, tert-butyl, tert-pentyl and tert-hexyl groups.

Examples of the acetal substituent represented by formula (2) include those having 2 to 8 carbon atoms, for example, 1-methoxyethyl, 1-ethoxyethyl, 1-n-propoxyethyl, 1-tert-butoxyethyl, 1-n-butoxyethyl, 1-isobutoxyethyl, 1-tert-pentoxyethyl, 1-cyclohexyloxyethyl, 1-(2'-n-butoxy)ethoxyethyl, 1-{n-(2'-ethyl)hexyl}oxyethyl, 1-(4'-acetoxymethyl-cyclohexylmethyloxy)ethyl, 1-{4'-(tert-butoxycarbonyloxymethyl)cyclohexylmethyloxy}ethyl, 2-methoxy-2-propyl, dimethoxymethyl, and diethoxymethyl groups.

Several illustrative, non-limiting, examples of the compound of formula (1) are given below:

tert-butyl 4,4-bis{4'-(1"-ethoxyethoxy)phenyl}valerate,
tert-butyl 4,4-bis{4'-(1"-tert-butoxyethoxy)phenyl}valerate,
tert-butyl 4,4-bis{4'-(2"-methoxy-2"-propoxy)phenyl}valerate,
tert-butyl 4,4-bis(4'-1"-n-butoxyethoxyphenyl)valerate,
tert-butyl 4,4-bis(4'-1"-isobutoxyethoxyphenyl)valerate,
tert-butyl 4,4-bis(4'-dimethoxymethoxyphenyl)valerate,
tert-butyl 4,4-bis(4'-diethoxymethoxyphenyl)valerate,
tert-butyl 3,3-bis(4'-1"-ethoxyethoxyphenyl)lactate,
tert-butyl 3,3-bis(4'-1"-ethoxyethoxyphenyl)valerate,
tert-butyl 2,2-bis(4-tert-butoxyphenyl)propionate,
tert-pentyl 4,4-bis{4'-(1"-ethoxyethoxy)phenyl}valerate, and
tert-pentyl 3,3-bis(4'-1"-ethoxyethoxyphenyl)lactate.

The compound of formula (1) can be easily synthesized in one step and at low cost by reacting a phenol derivative having a protected carboxyl group represented by formula (3) with a vinyl ether of formula (4) in the presence of an acid catalyst according to the following reaction scheme.

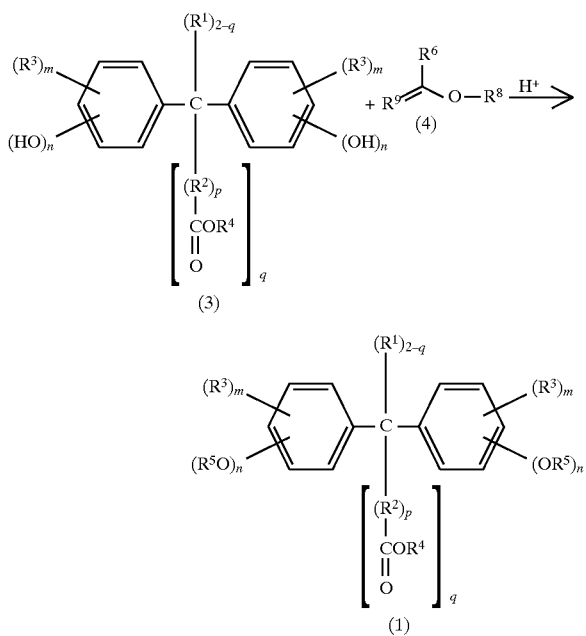

In these formulae, $R^1$ to $R^6$, p, q, m, and n are as defined above, and $R^9$ is a divalent group corresponding to $R^7$ with one hydrogen atom eliminated.

The above reaction is preferably carried out in an organic solvent such as methylene chloride and tetrahydrofuran (THF). Upon reaction of a carboxylate group-bearing phenol derivative of formula (3) with a vinyl ether of formula (4), these reactants are used in such amounts that 1 to 20 mol of the vinyl ether is available per mol of the OH group in the carboxylate group-bearing phenol derivative. The acid catalyst is preferably added in a proportion of 0.001 to 1 mol per mol of the OH group in the carboxylate group-bearing phenol derivative. Exemplary acid catalysts are trifluoromethanesulfonic acid, p-toluenesulfonic acid, sulfuric acid, hydrochloric acid, pyridinium p-toluene-sulfonate, pyridinium m-nitrobenzenesulfonate, and pyridinium sulfonate. Preferred reaction conditions include a temperature of 0° C. to room temperature and a time of 1 to 10 hours.

After the completion of reaction, the end compound of formula (1) is recovered by neutralizing the acid catalyst with an alkali, washing the solvent layer with water and concentrating it, followed by recrystallization or column fractionation.

The bisphenol carboxylic acid tertiary ester derivative of formula (1) according to the invention is advantageously used as a dissolution inhibitor in a three-component chemically amplified positive resist composition. One embodiment of the three-component chemically amplified positive resist composition containing the compound of formula (1) as a dissolution inhibitor is a composition comprising (A) an organic solvent,
(B) an alkali soluble resin,
(C) a photo-acid generator, and
(D) a dissolution inhibitor in the form of the bisphenol carboxylic acid tertiary ester derivative of formula (1).

Another embodiment is a composition comprising components (A) to (D) defined above and (E) another dissolution inhibitor other than the bisphenol carboxylic acid tertiary ester derivative of formula (1).

Examples of the organic solvent (A) used herein include ketones such as cyclohexanone and methyl 2-n-amyl ketone; alcohols such as 3-methoxybutanol, 3-methyl-3-methoxybutanol, 1-methoxy-2-propanol, and 1-ethoxy-2-propanol; ethers such as propylene glycol monomethyl ether, ethylene glycol monomethyl ether, propylene glycol monoethyl ether, ethylene glycol monoethyl ether, propylene glycol dimethyl ether, and diethylene glycol dimethyl ether (diglyme); and esters such as propylene glycol monomethyl ether acetate, propylene glycol monoethyl ether acetate, ethyl lactate, ethyl pyruvate, butyl acetate, methyl 3-methoxypropionate, and ethyl 3-ethoxypropionate, alone or in admixture of two or more.

The alkali-soluble resin (B) as a base resin may be selected from polyhydroxystyrenes and derivatives thereof, for example. Preferred derivatives of polyhydroxystyrene are those in which the hydrogen atoms of some hydroxyl (OH) groups are replaced by acid labile groups while copolymers of hydroxystyrene are also useful.

In the polyhydroxystyrene derivatives, the preferred acid labile group includes a tert-butyl group; substituted tert-butyl derivative groups such as tert-butoxycarbonyl and tert-butoxycarbonylmethyl groups; normal or branched chain acetal groups such as 1-ethoxyethyl, 1-propoxyethyl, 1-n-butoxyethyl, 1-isobutoxyethyl., 1-tert-butoxyethyl, and 1-tert-pentoxyethyl groups; and cyclic acetal groups such as tetrahydrofuranyl, tetrahydropyranyl, and 2-methoxy-tetrahydropyranyl groups.

The copolymers of hydroxystyrene include copolymers of hydroxystyrene with styrene, copolymers of hydroxystyrene with tert-butyl acrylate, copolymers of hydroxystyrene with tert-butyl methacrylate, copolymers of hydroxystyrene with maleic anhydride, and copolymers of hydroxystyrene with di-tert-butyl maleate.

The polyhydroxystyrene or derivatives thereof should preferably have a weight average molecular weight of 3,000 to 100,000. Below 3,000, film formation and resolution would be poor. Above 100,000, resolution would be poor.

Any of well-known photo-acid generators may be used as component (C). One preferred class of photo-acid generators consists of onium salts of the following general formula (5):

wherein R groups, which may be identical or different, are selected from substituted or unsubstituted aromatic groups, M is sulfonium or iodonium, Y is p-toluenesulfonate, trifluoromethanesulfonate or normal, branched or cyclic alkylsulfonate having 1 to 20 carbon atoms, and letter $\underline{a}$ is 2 or 3. Examples of the aromatic group represented by R include phenyl, tert-butoxyphenyl, tert-butylphenyl, tert-butoxycarbonyloxyphenyl, tert-butoxycarbonylmethoxyphenyl, tert-butyldimethylsilyloxyphenyl, tetrahydrofuranyloxyphenyl, 1-ethoxyethoxyphenyl, 1-propoxyethoxyphenyl, and 1-tert-butoxyethoxyphenyl groups. Other useful examples of the photo-acid generator are pyrogallolsulfonic acid ester derivatives such as 1,2,3-tris(methanesulfonyloxy)benzene, 1,2,3-tris(trifluoromethanesulfonyloxy)benzene, 1,2,3-tris(n-butanesulfonyloxy)benzene, 1,2,3-tris(p-toluenesulfonyloxy)benzene, and 1,2,3-tris((+)10-camphorsulfonyloxy)benzene;

nitrobenzylsulfonic acid derivatives such as 2-nitrobenzyltosylate, 2,6-dinitrobenzyltosylate, and 2,4-dinitrobenzyltosylate;

diazonaphthoquinone sulfonic acid ester derivatives such as 3,4,5-tris(5-diazonaphthoquinonesulfonyloxy)benzophenone and 3,4,5-tris(4-diazonaphthoquinonesulfonyloxy)benzophenone;

α, α'-bisaryl or bisalkylsulfonyldiazomethane derivatives such as α, α'-bisphenylsulfonyldiazomethane, α, α'-bis(p- tert-butylphenylsulfonyl)diazomethane, α, α'-bis(p-tert-butoxyphenylsulfonyl)diazomethane, and α, α'-biscyclohexylsulfonyldiazomethane; and N-sulfonyloxyimide derivatives such as N-trifluoromethanesulfonyl phthalimide; N-(p-toluenesulfonyloxy) phthalimide, N-trifluoromethanesulfonyloxysuccinimide, N-(p-toluenesulfonyloxy)succinimide, and N-camphorsulfonyloxynaphthalimide.

Exemplary compounds suitable as a photo-acid generator are shown below.

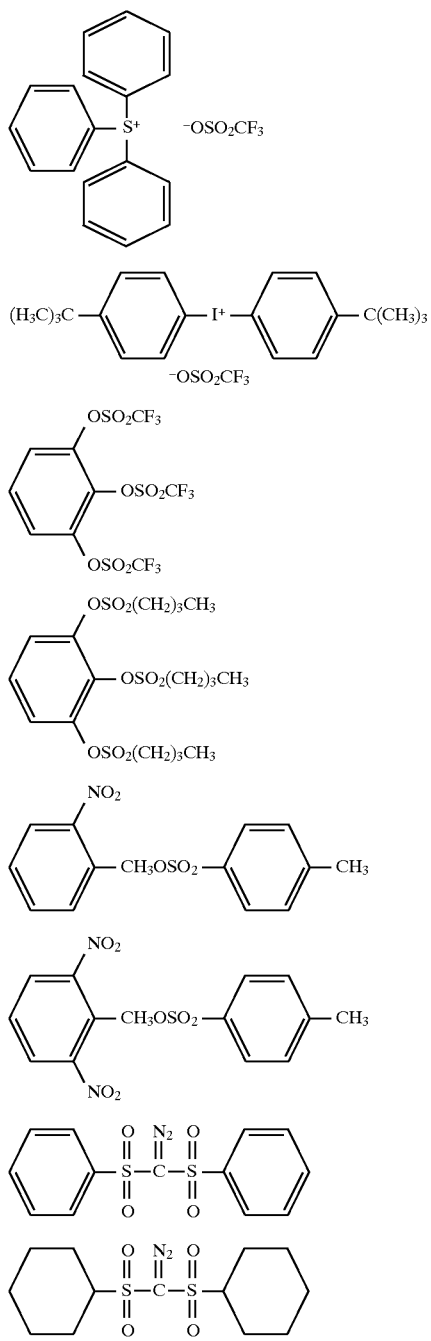

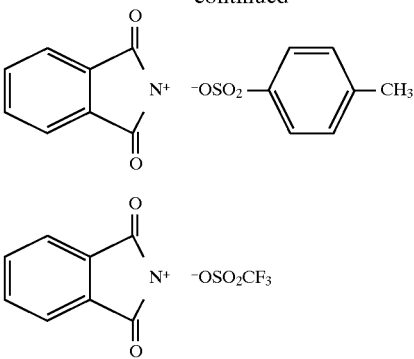

According to the invention, the bisphenol carboxylic acid tertiary ester derivative of formula (1) is blended as the dissolution inhibitor (D). If desired, another dissolution inhibitor may be blended as component (E) in addition to the dissolution inhibitor of formula (1). The other dissolution inhibitor (E) may be any of low molecular weight compounds and polymers which have in a molecule at least one group decomposable with acid. Exemplary low molecular weight compounds are bisphenol-A derivatives and carbonate ester derivatives. Preferred are bisphenol-A derivatives wherein the hydrogen atom of a hydroxyl group of bisphenol-A is replaced by a tert-butyl derivative substituent such as tert-butoxy, tert-butoxycarbonyl and tert-butoxycarbonylmethyl groups; a normal or branched chain acetal group such as 1-ethoxyethyl, 1-propoxyethyl, 1-n-butoxyethyl, 1-isobutoxyethyl, 1-tert-butoxyethyl, and 1-tert-amyloxyethyl groups; or a cyclic acetal group such as tetrahydrofuranyl and tetrahydropyranyl groups. Examples of the polymeric dissolution inhibitor include copolymers of p-butoxystyrene and tert-butyl acrylate and copolymers of p-butoxystyrene and maleic anhydride. These copolymers should preferably have a weight average molecular weight of 500 to 10,000.

Preferably, the three-component chemically amplified positive resist composition of the invention contains 50 to 700 parts, especially 250 to 500 parts of the organic solvent (A), 70 to 90 parts, especially 75 to 85 parts of the alkali soluble resin (B), and 0.5 to 15 parts, especially 2 to 8 parts of the photo-acid generator (C). It is noted that all parts are by weight throughout the disclosure and the amount of the remaining components is expressed relative to these amounts of components (A) to (C). The amount of the dissolution inhibitor (D) or compound of formula (1) blended is 5 to 40 parts, especially 10 to 25 parts. Less than 5 parts of dissolution inhibitor (D) would be ineffective for inhibiting dissolution whereas more than 40 parts of dissolution inhibitor (D) would adversely affect the heat resistance of the resist film. The amount of the other dissolution inhibitor (E), if blended, is 5 to 40 parts, especially 10 to 25 parts.

The resist composition of the invention may further contain various additives, for example, a carboxylic acid derivative and nitrogenous compound for improving PED stability and dimensional precision, a surface-active agent for facilitating coating, and a light-absorbing agent for reducing irregular reflection from the substrate.

Examples of the carboxylic acid derivative include 4-hydroxyphenylacetic acid, 3-hydroxyphenylacetic acid, 2-hydroxyphenylacetic acid, 3-(4-hydroxyphenyl)propionic acid, 3-(2-hydroxyphenyl)propionic acid, 2,5-dihydroxyphenylacetic acid, 3,4-dihydroxyphenylacetic acid, 1,2-phenylenediacetic acid, 1,3-phenylenediacetic acid, 1,4-phenylenediacetic acid, 1,2-phenylenedioxydiacetic acid, 1,4-phenylenedipropanoic acid, benzoic acid, 4,4-(4-hydroxyphenyl)valeric acid, 4-tert-butoxyphenylacetic acid, 4-(4-hydroxyphenyl)lactic acid, 3,4-dihydroxymandelic acid, and 4-hydroxymandelic acid. The amount of the carboxylic acid derivative blended in the resist composition of the invention is preferably 0.1 to 15 parts, especially 1 to 10 parts.

Typical nitrogenous compounds are amine and amide compounds having a boiling point of 150° C. or higher. Examples include aniline, N-methylaniline, N,N-dimethylaniline, o-toluidine, m-toluidine, p-toluidine, 2,4-lutidine, quinoline, isoquinoline, formamide, N-methylformamide, N,N-dimethylformamide, acetamide, N-methylacetamide, N,N-dimethylacetamide, 2-pyrrolidone, N-methylpyrrolidone, imidazole, α-picoline, β-picoline, γ-picoline, o-aminobenzoic acid, m-aminobenzoic acid, p-aminobenzoic acid, 1,2-phenylenediamine, 1,3-phenylenediamine, 1,4-phenylenediamine, 2-quinolinecarboxylic acid, 2-amino-4-nitrophenol, and triazines such as 2-(p-chlorophenyl)-4,6-trichloromethyl-s-triazine. Preferred among others are pyrrolidone, N-methylpyrrolidone, o-, m- and p-aminobenzoic acid, 1,2-, 1,3- and 1,4-phenylenediamine. The amount of the nitrogenous compound blended in the resist composition of the invention is preferably 0.05 to 4 parts, especially 0.1 to 1 part.

Examples of the surfactant include perfluoroalkylpolyoxyethylene ethanols, fluorinated alkyl esters, perfluoroalkylamine oxides, and perfluoroalkyl EO addition products. Examples of the light-absorbing agent include diaryl sulfoxides, diaryl sulfones, 9,10-dimethylanthracene, and 9-fluorenone.

Any well-known lithography may be applied with respect to the use of a positive resist composition of the invention and light exposure. The resist composition of the invention is especially suitable for fine patterning with deep-UV radiation of 254 to 193 nm and electron beams.

A resist material containing a bisphenol carboxylic acid tertiary ester derivative of formula (1) as a dissolution inhibitor according to the invention has many advantages. Since the dissolution inhibitor has a highly reactive acetal group as an acid labile group, quick coupling-off of the acid labile group takes place after exposure. The dissolution inhibitor itself is less alkali soluble while its acid decomposition product is a phenol derivative having a carboxylic acid group featuring high alkali solubility. This leads to a high dissolution contrast. Then the resist material containing a bisphenol carboxylic acid tertiary ester derivative of formula (1) as a dissolution inhibitor according to the invention is a useful chemically amplified positive working resist material which is highly sensitive to actinic radiation such as deep-UV radiation, electron beam and X-ray, especially KrF excimer laser light and can be developed with aqueous base to form a pattern. The inventive resist material has improved sensitivity, resolution and plasma etching resistance while the resulting resist pattern is fully resistant to heat.

EXAMPLE

Examples of the present invention are given below by way of illustration and not by way of limitation. All parts are by weight.

Synthesis Example 1

Synthesis of tert-butyl 4,4-bis(4'-(1"-ethoxyethoxy)phenyl)valerate

In a solvent mixture of 75 grams of THF and 75 grams of methylene chloride was dissolved 30.9 grams (0.09 mol) of tert-butyl 4,4-bis(4'-hydroxyphenyl)valerate. With stirring, 38.9 grams (0.54 mol) of ethyl vinyl ether was added dropwise while the mixture was cooled with an ice bath so that the temperature would not exceed 10° C. After the reaction mixture was stirred for a further 20 minutes, 2.0 grams (8 mmol) of p-toluenesulfonic acid monohydrate was added and dissolved, with the mixture kept cooled so that the reaction temperature would not exceed 10° C. The ice bath was removed and the reaction mixture was stirred for 1.5 hours at room temperature. The reaction solution was cooled with ice, and 201 grams of a 0.6% sodium hydrogen carbonate aqueous solution was added to neutralize the acid for terminating the reaction. The organic layer was separated and the solvent was distilled off in vacuo, obtaining an oily product. The oily product was purified by silica gel column chromatography (eluting solvent: chloroform), isolating tert-butyl 4,4-bis(4'-(1"-ethoxyethoxy)phenyl)valerate. Amount 24.1 grams, yield 54.9%, purity 95.7%.

The thus obtained tert-butyl 4,4-bis(4'-(1"-ethoxy-ethoxy)phenyl)valerate was analyzed by nuclear magnetic resonance (NMR) spectroscopy, infrared (IR) spectroscopy, and elemental analysis, with the results shown below.

$$H_3CH_2CO-\underset{H}{\overset{CH_3}{\underset{|}{C}}}-O-\text{\textlangle}\text{\textrangle}-\underset{\underset{\underset{O}{\overset{||}{C}-O-C(CH_3)_3}}{\overset{CH_2f}{|}}}{\overset{CH_3}{\underset{|}{\overset{|}{C}}}}-\text{\textlangle}\text{\textrangle}-O-\underset{H}{\overset{CH_3}{\underset{|}{C}}}-OCH_2CH_3$$

with labels d, c above; j, i, CH₂e; g, a; h, b $^1$H-NMR: CDCl$_3$, δ (ppm)

| | | |
|---|---|---|
| (a) 1.17 | triplet | 6H |
| (b) 1.40 | singlet | 9H |
| (c) 1.46 | doublet | 6H |
| (d) 1.55 | singlet | 3H |
| (e) 1.96–2.03 | triplet | 2H |
| (f) 2.30–2.36 | triplet | 2H |
| (g) 3.44–3.83 | multiplet | 4H |
| (h) 5.30–5.34 | quadruplet | 2H |
| (i) 6.86 | doublet | 4H |
| (j) 7.08 | doublet | 4H |

IR: cm$^{-1}$ 2977, 2935, 1727, 1608, 1508, 1369, 1365, 1297, 1295, 1243, 1182, 1151, 1078, 1047, 943, 902, 837

Elemental analysis for $C_{29}H_{42}O_6$: %

Calcd. C: 71.6 H: 8.7

Found C: 71.7 H: 8.7

Synthesis Example 1A

Synthesis Example 1 was repeated except that pyridinium p-toluenesulfonate was used instead of p-toluenesulfonic acid monohydrate and reaction was effected for 8 hours at room temperature, obtaining the same tert-butyl 4,4-bis(4'-(1"-ethoxyethoxy)phenyl)valerate as in Synthesis Example 1 in a yield of 71.9% and a purity of 96.9%.

Synthesis Example 2

Synthesis Example 1 was repeated except that n-propyl vinyl ether was used instead of ethyl vinyl ether, obtaining tert-butyl 4,4-bis(4'-(1"-n-propoxyethoxy)phenyl)valerate in a yield of 78.3% and a purity of 98.6%.

Synthesis Example 3

Synthesis Example 1 was repeated except that tert-butyl vinyl ether was used instead of ethyl vinyl ether, obtaining tert-butyl 4,4-bis(4'-(1"-tert-butoxyethoxy)phenyl)valerate in a yield of 76.6% and a purity of 98.4%.

The thus obtained tert-butyl 4,4-bis(4'-(1"-tert-butoxyethoxy)phenyl)valerate was analyzed by NMR spectroscopy, IR spectroscopy, and elemental analysis, with the results shown below.

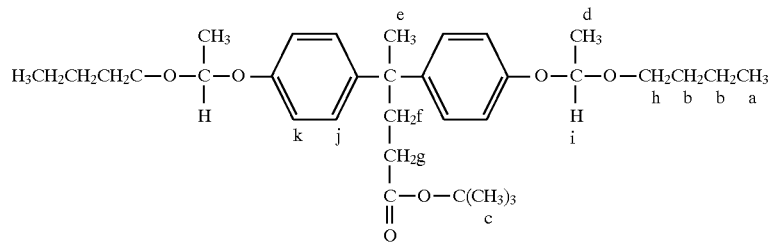

$^1$H-NMR: CDCl$_3$, δ (ppm)

| (a) 1.22 | singlet | 18H |
|---|---|---|
| (b) 1.39 | singlet | 9H |
| (c) 1.39–1.41 | doublet | 6H |
| (d) 1.54 | singlet | 3H |
| (e) 2.02 | triplet | 2H |
| (f) 2.30 | triplet | 2H |
| (g) 5.46–5.52 | quadruplet | 2H |
| (h) 6.78, 6.81 | doublet | 4H |
| (i) 7.04, 7.07 | doublet | 4H |

IR: cm$^{-1}$
2978, 2935, 1727, 1608, 1578, 1508, 1473, 1458, 1392, 1367, 1248, 1151, 1124, 1068, 1012, 970, 903, 850, 756
Elemental analysis for C$_{33}$H$_{50}$O$_6$: %
Calcd. C: 73.0 H: 9.3
Found C: 73.0 H: 9.3

Synthesis Example 4

Synthesis Example 1 was repeated except that n-butyl vinyl ether was used instead of ethyl vinyl ether, obtaining tert-butyl 4,4-bis(4'-(1"-n-butoxyethoxy)phenyl)valerate in a yield of 55.5% and a purity of 95.9%.

The thus obtained tert-butyl 4,4-bis(4'-(1"-n-butoxyethoxy)phenyl)valerate was analyzed by NMR spectroscopy, IR spectroscopy, and elemental analysis, with the results shown below.

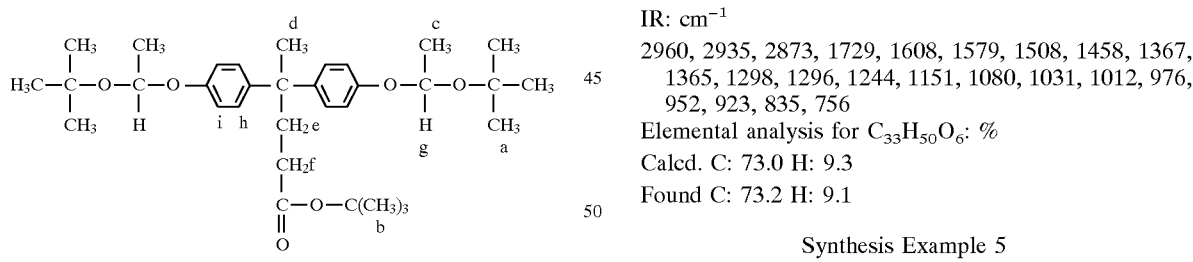

$^1$H-NMR: CDCl$_3$, δ (ppm)

| (a) 0.83–0.93 | triplet | 6H |
|---|---|---|
| (b) 1.22–1.37 | multiplet | 8H |
| (c) 1.39 | singlet | 9H |
| (d) 1.45 | doublet | 6H |
| (e) 1.54 | singlet | 3H |
| (f) 2.02 | triplet | 2H |
| (g) 2.30 | triplet | 2H |
| (h) 3.38–3.73 | multiplet | 4H |
| (i) 5.30–5.36 | quadruplet | 2H |
| (j) 6.85, 6.88 | doublet | 4H |
| (k) 7.05, 7.09 | doublet | 4H |

IR: cm$^{-1}$
2960, 2935, 2873, 1729, 1608, 1579, 1508, 1458, 1367, 1365, 1298, 1296, 1244, 1151, 1080, 1031, 1012, 976, 952, 923, 835, 756
Elemental analysis for C$_{33}$H$_{50}$O$_6$: %
Calcd. C: 73.0 H: 9.3
Found C: 73.2 H: 9.1

Synthesis Example 5

Synthesis Example 1 was repeated except that isobutyl vinyl ether was used instead of ethyl vinyl ether, obtaining tert-butyl 4,4-bis(4'-(1"-isobutoxyethoxy)phenyl)valerate in a yield of 37.4% and a purity of 96.9%.

The thus obtained tert-butyl 4,4-bis(4'-(1"-isobutoxyethoxy)phenyl)valerate was analyzed by NMR spectroscopy, IR spectroscopy, and elemental analysis, with the results shown below.

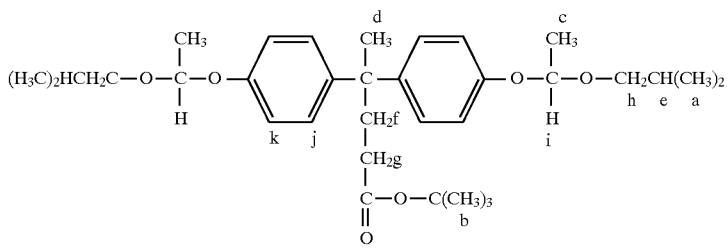

$^1$H-NMR: CDCl$_3$, δ (ppm)

| | | |
|---|---|---|
| (a) 0.87 | doublet | 12H |
| (b) 1.40 | singlet | 9H |
| (c) 1.45, 1.47 | doublet | 6H |
| (d) 1.55 | singlet | 3H |
| (e) 1.63–1.86 | septet | 2H |
| (f) 1.96–2.02 | triplet | 2H |
| (g) 2.30–2.33 | triplet | 2H |
| (h) 3.15–3.48 | multiplet | 4H |
| (i) 5.30–5.36 | quadruplet | 2H |
| (j) 6.85–6.89 | doublet | 4H |
| (k) 7.95–7.08 | doublet | 4H |

IR: cm$^{-1}$
2958, 2873, 1729, 1608, 1579, 1508, 1469, 1384, 1367, 1295, 1243, 1151, 1080, 1034, 1014, 1012, 927, 910, 835, 756

Elemental analysis for $C_{33}H_{50}O_6$: %

Calcd. C: 73.0 H: 9.3

Found C: 72.9 H: 9.3

Synthesis Example 6

Synthesis Example 1 was repeated except that 2-methoxypropene was used instead of ethyl vinyl ether, obtaining tert-butyl 4,4-bis(4'-(1"-methoxy-1"-methylethoxy)phenyl)valerate in a yield of 45.2% and a purity of 97.2%.

Synthesis Example 7

Synthesis of tert-butyl 4,4-bis(4'-dimethoxymethoxyphenyl)valerate

A four-necked flask equipped with a Dimroth condenser was charged with 45.5 grams (0.13 mol) of tert-butyl 4,4-bis(4'-hydroxyphenyl)valerate and 388 grams (3.6 mol) of methyl ortho-formate, then with 0.6 grams of p-toluenesulfonic acid, and heated at 130° C. for 3 hours for reaction while the by-produced methanol was distilled off through the Dimroth condenser. The reaction solution was cooled to room temperature, combined with 410 grams of a 0.5% potassium carbonate aqueous solution and stirred. Diethyl ether, 200 grams, was added to the reaction solution, from which the organic layer was extracted. By distilling off the solvent and purifying by silica gel column chromatography (eluting solvent: chloroform), there was isolated tert-butyl 4,4-bis(4'-dimethoxymethoxyphenyl)valerate as a colorless clear liquid. Amount 57.5 grams, yield 90.2%, purity 98.2%.

Synthesis Example 8

Synthesis Example 7 was repeated except that ethyl ortho-formate was used instead of methyl ortho-formate, obtaining tert-butyl 4,4-bis(4'-diethoxymethoxyphenyl)valerate in a yield of 89.5% and a purity of 97.2%.

Examples 1–12 and Comparative Examples 1–10

Liquid resist compositions were prepared by dissolving an alkali soluble resin, a photoacid generator, and a dissolution inhibitor in a solvent in accordance with the formulation shown in Tables 1 and 2. Each of the compositions was passed through a 0.2-μm Teflon® filter.

The alkali soluble resins used were a polyhydroxystyrene in which the hydrogen atoms of some hydroxyl groups are protected with tert-butoxycarbonyl groups, designated Polym.1, a polyhydroxystyrene in which the hydrogen atoms of some hydroxyl groups are protected with tetrahydrofuranyl groups, designated Polym.2, and a polyhydroxystyrene in which the hydrogen atoms of some hydroxyl groups are protected with 1-ethoxyethyl groups, designated Polym.3.

The photoacid generators used were an onium salt designated PAG.1, pyrogallolsulfonic acid derivative designated PAG.2, benzylsulfonic acid derivative designated PAG.3, bisalkylsulfonyldiazomethane derivative designated PAG.4, and N-sulfonyloxyimide derivative designated PAG.5.

The dissolution inhibitors used were DRI.1 to DRI.7 selected from 4,4'-bis(4-hydroxyphenyl)valeric acid derivatives, 2,2'-bis(4-tert-butoxycarbonyloxyphenyl)propane, and 4,4'-bis(4-hydroxyphenyl)acetic acid derivatives.

Polym.1 to Polym.3, PAG.1 to PAG.5, and DRI.1 to DRI.7 are shown below.

The solvents used were 1-ethoxy-2-propanol (EIPA), a mixture of 85% by weight ethyl lactate and 15% by weight butyl acetate (EL/BA), propylene glycol monomethyl ether acetate (PGMEA), and N-methylpyrrolidone (NMP).

Each liquid resist composition was then spin coated onto a silicon wafer to form a coating of 0.7 μm thick. With the silicon wafer rested on a hot plate at 100° C., the coating was pre-baked for 120 seconds. The film was exposed to a pattern of light by means of an excimer laser stepper model NSR-2005EX (manufactured by Nikon K.K., numerical aperture NA=0.5), baked at 90° C. for 90 seconds, and developed with an aqueous solution of 2.38% tetramethylammonium hydroxide, obtaining a positive pattern.

The resulting resist pattern was evaluated as follows. First, a sensitivity (Eth value) was determined. Provided that the exposure quantity with which the top and bottom of a 0.30-μm line-and-space pattern were resolved at 1:1 was the optimum exposure (sensitivity Eop), the minimum line width of a line-and-space pattern which was recognized separate at this exposure was the resolution of a test resist. The configuration of the resist pattern resolved was observed under a scanning electron microscope. Whether or not scum generated was examined by an observation through a scanning electron microscope. The resist material was also examined for sensitivity stability by allowing it to stand at room temperature (23° C.) until the change of Eth exceeded 10% of the initial value. A higher day count indicates higher stability.

The results are shown in Tables 1 and 2.

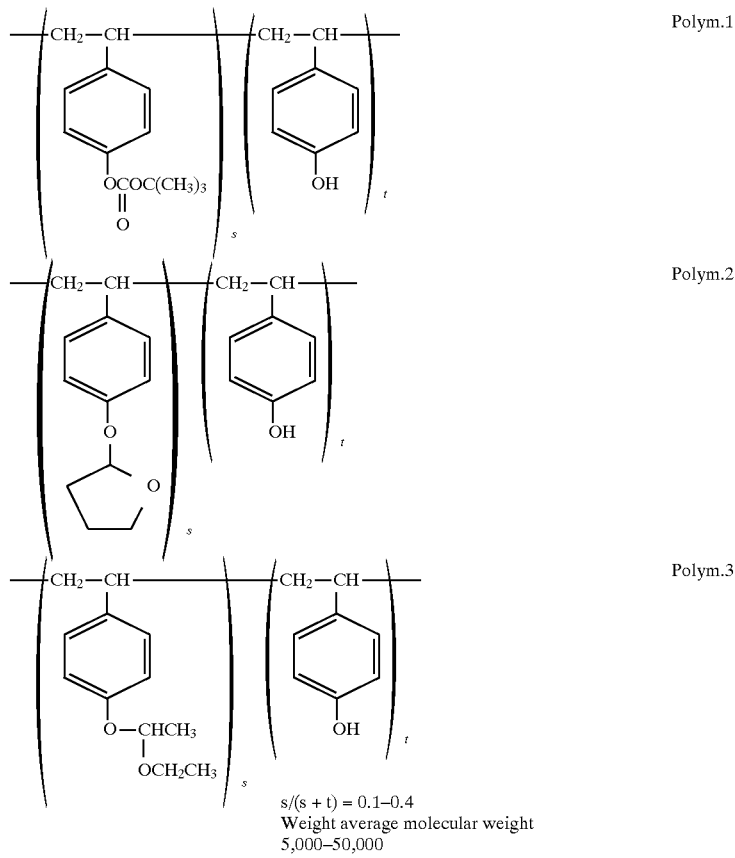

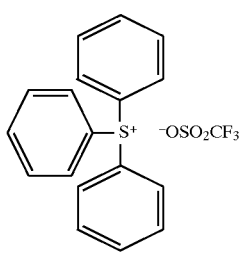

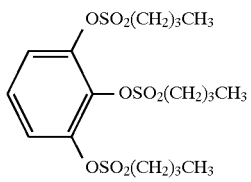

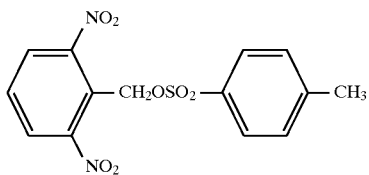

-continued
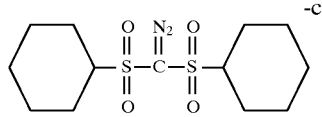 PAG.4
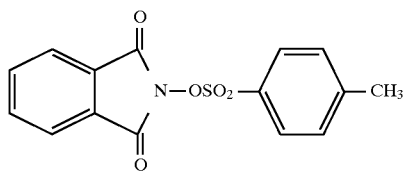 PAG.5
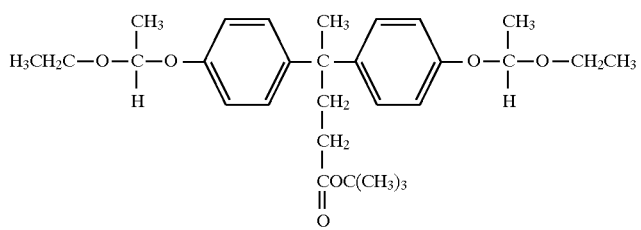 DRI.1
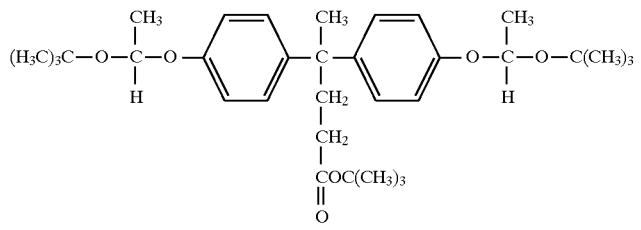 DRI.2

TABLE 2

| Comparative Example | Alkali soluble resin | Photoacid generator | Dissolution inhibitor | Solvent | Eop (mJ/cm$^2$) | Resolution ($\mu$m) | Pattern shape | Scum | Sensitivity stability (days) |
|---|---|---|---|---|---|---|---|---|---|
| 1 | Polym.1(80) | PAG.1(5) | DRI.4(15) | EIPA (500) | 4.0 | 0.28 | tapered* | scum | ≧180 |
| 2 | Polym.2(80) | PAG.1(1) PAG.2(4) | DRI.4(15) | EIPA (500) | 8.5 | 0.28 | tapered* | scum | ≧180 |
| 3 | Polym.3(80) | PAG.1(1) PAG.4(4) | DRI.4(15) | EIPA (500) | 10.0 | 0.28 | tapered* | scum | ≧180 |
| 4 | Polym.1(30) Polym.2(50) | PAG.1(2) PAG.5(2) | DRI.4(15) | EL/BA (500) | 9.0 | 0.28 | tapered* | scum | ≧180 |
| 5 | Polym.1(40) Polym.3(40) | PAG.1(5) | DRI.5(10) | PGMEA (450) | 8.5 | 0.26 | rectangular | scum | ≧180 |
| 6 | Polym.1(80) | PAG.1(5) | DRI.6(15) | EIPA (500) | 3.5 | 0.28 | round | none | ~15 |
| 7 | Polym.1(80) | PAG.1(5) | DRI.6(15) | EL/BA (500) | 3.0 | 0.28 | round | none | ~10 |
| 8 | Polym.1(30) Polym.2(50) | PAG.1(5) | DRI.6(15) | PGMEA (450) | 3.0 | 0.28 | round | none | ~15 |
| 9 | Polym.1(80) | PAG.1(5) | DRI.7(15) | EIPA (500) | 9.5 | 0.28 | round | none | ~15 |
| 10 | Polym.1(20) Polym.3(60) | PAG.3(1) PAG.4(2) | — | PGMEA (450) | 6.0 | 0.28 | round | none | ≧180 |

*slightly forward tapered

It is evident that chemically amplified positive resist compositions within the scope of the invention have high sensitivity and stability thereof, high resolution and rectangular pattern definition and are free of scum.

Japanese Patent Application No. 263457/1995 is incorporated herein by reference.

Although some preferred embodiments have been described, many modifications and variations may be made thereto in the light of the above teachings. It is therefore to be understood that within the scope of the appended claims, the invention may be practiced otherwise than as specifically described.

We claim:

1. A bisphenol carboxylic acid tertiary ester compound of the following formula (1):

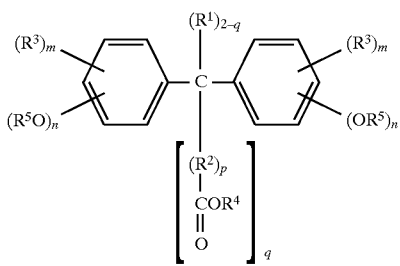

wherein each of $R^1$ and $R^3$ is a hydrogen atom, normal or branched alkyl group, normal or branched alkoxy group, or normal or branched alkoxyalkyl group, $R^2$ is a normal or branched alkylene group, $R^4$ is a tertiary alkyl group, $R^5$ is an acetal substituent of the following formula (2):

wherein $R^6$ is a hydrogen atom, normal or branched alkyl group, normal or branched alkoxy group, or normal or branched alkoxyalkyl group, which may contain a carbonyl group in their molecular chain, $R^7$ is a normal or branched alkyl group, normal or branched alkoxy group, or normal or branched alkoxyalkyl group, which may contain a carbonyl group in their molecular chain, $R^8$ is a normal or branched alkyl group, or normal or branched alkoxyalkyl group, which may contain a carbonyl group in their molecular chain, and letter p is an integer of 0 to 5, q is equal to 1 or 2, m and n are integers satisfying m≧0, n≧1, and m+n≦5.

2. A chemically amplified positive resist composition comprising the bisphenol carboxylic acid tertiary ester compound of claim 1 as a dissolution inhibitor.

3. A chemically amplified positive resist composition comprising (A) an organic solvent, (B) an alkali soluble resin, (C) a photo-acid generator, and (D) a dissolution inhibitor in the form of the bisphenol carboxylic acid tertiary ester compound of claim 1.

4. The chemically amplified positive resist composition of claim 3 wherein the alkali soluble resin (B) is a polyhydroxystyrene in which the hydrogen atoms of some hydroxyl groups are replaced by acid labile groups and has a weight average molecular weight of 3,000 to 100,000.

5. A chemically amplified positive resist composition comprising (A) an organic solvent, (B) an alkali soluble resin, (C) a photo-acid generator, (D) a dissolution inhibitor in the form of the bisphenol carboxylic acid tertiary ester compound of claim 1, and (E) another dissolution inhibitor.

6. The chemically amplified positive resist composition of claim 5 wherein the alkali soluble resin (B) is a polyhydroxystyrene in which the hydrogen atoms of some hydroxyl groups are replaced by acid labile groups and has a weight average molecular weight of 3,000 to 100,000.

7. The bisphenol carboxylic acid tertiary ester compound of claim 1, wherein the normal or branched alkyl groups present are of 1 to 8 carbon atoms, the normal or branched alkoxy groups present are of 1 to 8 carbon atoms, the normal or branched alkoxyalkyl groups present are of 3 to 10 carbon atoms, the normal or branched alkylene groups present are of 1 to 8 carbon atoms and the tertiary alkyl groups present are of 4 to 8 carbon atoms.

8. The bisphenol carboxylic acid tertiary ester compound of claim 1, wherein the acetal substituent(s) of the formula (2) has 2 to 8 carbon atoms.

9. The bisphenol carboxylic acid tertiary ester compound of claim 1, wherein the acetal substituent(s) of the formula (2) are selected from the group consisting of 1-methoxyethyl, 1-ethoxyethyl, 1-n-propoxyethyl, 1-tert-butoxyethyl, 1-n-butoxyethyl, 1-isobutoxyethyl, 1-tert-pentoxyethyl, 1-cyclohexyloxyethyl, 1-(2'-n-butoxy)ethoxyethyl, 1-{n-(2'-ethyl)hexyl}oxyethyl, 1-(4'-acetoxymethyl-cyclohexylmethyloxy}ethyl, 1-{4'-(tert-butoxycarbonyloxymethyl)cyclohexylmethyloxy}ethyl, 2-methoxy-2-propyl, dimethoxymethyl, and diethoxymethyl groups.

10. The bisphenol carboxylic acid tertiary ester compound of claim 1, wherein the compound is tert-butyl 4,4-bis{4'-(1"-ethoxyethoxy)phenyl}valerate, tert-butyl 4,4-bis{4'-(1"-tert-butoxyethoxy)phenyl}valerate, tert-butyl 4,4-bis{4'-(2"-methoxy-2"-propoxy)phenyl}valerate, tert-butyl 4,4-bis(4'-1"-n-butoxyethoxyphenyl)valerate, tert-butyl 4,4-bis(4'-1"-isobutoxyethoxyphenyl)valerate, tert-butyl 4,4-bis(4'-dimethoxymethoxyphenyl)valerate, tert-butyl 4,4-bis(4'-diethoxymethoxyphenyl)valerate, tert-butyl 3,3-bis(4'-1"-ethoxyethoxyphenyl)lactate, tert-butyl 3,3-bis(4'-1"-ethoxyethoxyphenyl)valerate, tert-butyl 2,2-bis(4-tert-butoxyphenyl)propionate, tert-pentyl 4,4-bis{4'-(1"-ethoxyethoxy)phenyl}valerate, and tert-pentyl 3,3-bis(4'-1"-ethoxyethoxyphenyl)lactate.

11. The composition of claim 4, wherein at least one acid labile group is a tert-butyl; tert-butoxycarbonyl; tert-butoxycarbonylmethyl; normal or branched chain acetal; or cyclic acetal group.

12. The composition of claim 6, wherein at least one acid labile group is a tert-butyl; tert-butoxycarbonyl; tert-butoxycarbonylmethyl; normal or branched chain acetal; or cyclic acetal group.

13. The composition of claim 3 which contains 50 to 700 parts by weight of (A), 70 to 90 parts by weight of (B), 0.5 to 15 parts by weight of (C) and 5 to 40 parts by weight of (D).

14. The composition of claim 5 which contains 50 to 700 parts by weight of (A), 70 to 90 parts by weight of (B), 0.5 to 15 parts by weight of (C), 5 to 40 parts by weight of (D), and 5 to 40 parts by weight of (E).

* * * * *